United States Patent [19]
LeMarie, III et al.

[11] Patent Number: 5,366,477
[45] Date of Patent: Nov. 22, 1994

[54] ACTUATING FORCES TRANSMISSION LINK AND ASSEMBLY FOR USE IN SURGICAL INSTRUMENTS

[75] Inventors: Norman J. LeMarie, III, Taunton; Francis J. DiFrancesco, Foxboro; Paul DiCarlo, E. Falmouth; Peter D. Naugler, Manchester; George J. Sikora, Brockton, all of Mass.

[73] Assignee: American Cyanamid Company, Wayne, N.J.

[21] Appl. No.: 779,431

[22] Filed: Oct. 17, 1991

[51] Int. Cl.⁵ ............................................. A61B 17/24
[52] U.S. Cl. ................................ 606/208; 606/170; 403/91; 403/336
[58] Field of Search ............... 606/170, 174, 184, 205, 606/206, 207, 208, 209; 128/751; 74/107, 567; 403/13, 14, 91, 92, 93, 94, 95, 381, 382, 315, 43, 44, 355, 336; 37/457, 458

[56] References Cited

U.S. PATENT DOCUMENTS

| | | | |
|---|---|---|---|
| 2,518,994 | 8/1950 | Miller | 606/205 |
| 3,357,422 | 12/1967 | Creelman | 606/170 |
| 3,419,295 | 12/1968 | Small | 403/92 X |
| 3,814,102 | 6/1974 | Thal | 606/207 |
| 4,243,047 | 1/1981 | Olsen | 128/751 |
| 4,712,545 | 12/1987 | Honkanen | 128/305 |
| 4,887,929 | 12/1989 | Hale | 403/328 |
| 4,898,157 | 2/1990 | Messroghli et al. | 606/147 |
| 5,035,248 | 7/1991 | Zinnecker | 128/751 |
| 5,071,430 | 12/1991 | de Salis et al. | 606/219 |
| 5,133,736 | 7/1992 | Bales, Jr. et al. | 606/205 |
| 5,178,625 | 1/1993 | Groshong | 606/159 |

OTHER PUBLICATIONS

Laproscopic Cholecystectomy Instruments, Stryker Endoscopy Brochure—Jan., 1991?.

Primary Examiner—Edgar S. Burr
Assistant Examiner—Christopher A. Bennett
Attorney, Agent, or Firm—D. E. Denninger

[57] ABSTRACT

A link, and assembly and instrument using same, for transmitting actuating forces from an actuating member to a work member. The link includes a link body having a distal end and a proximal end. The distal end of the link body is movably interconnected with the work member by a distal interconnection element such as an arcuate groove-and-flange assembly, and is interconnected at its proximal end to an actuating member by a proximal pivotal interconnection element. The proximal element transmits a first actuating force from the actuating member to the work member. A shoulder, disposed on the link body preferably between the distal and proximal elements for interconnecting, engages the actuating member when a second, greater actuating force is applied to the actuating member in a direction opposite to that of the first actuating force. The greater force is thereby transmitted fully to the work member. The link assembly preferably includes a spacer member to assist positioning of the actuating member.

15 Claims, 10 Drawing Sheets

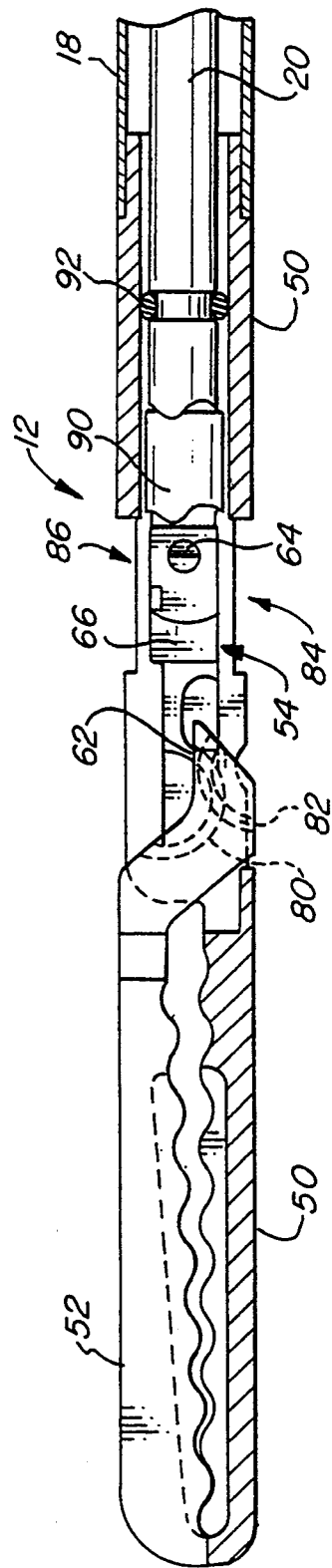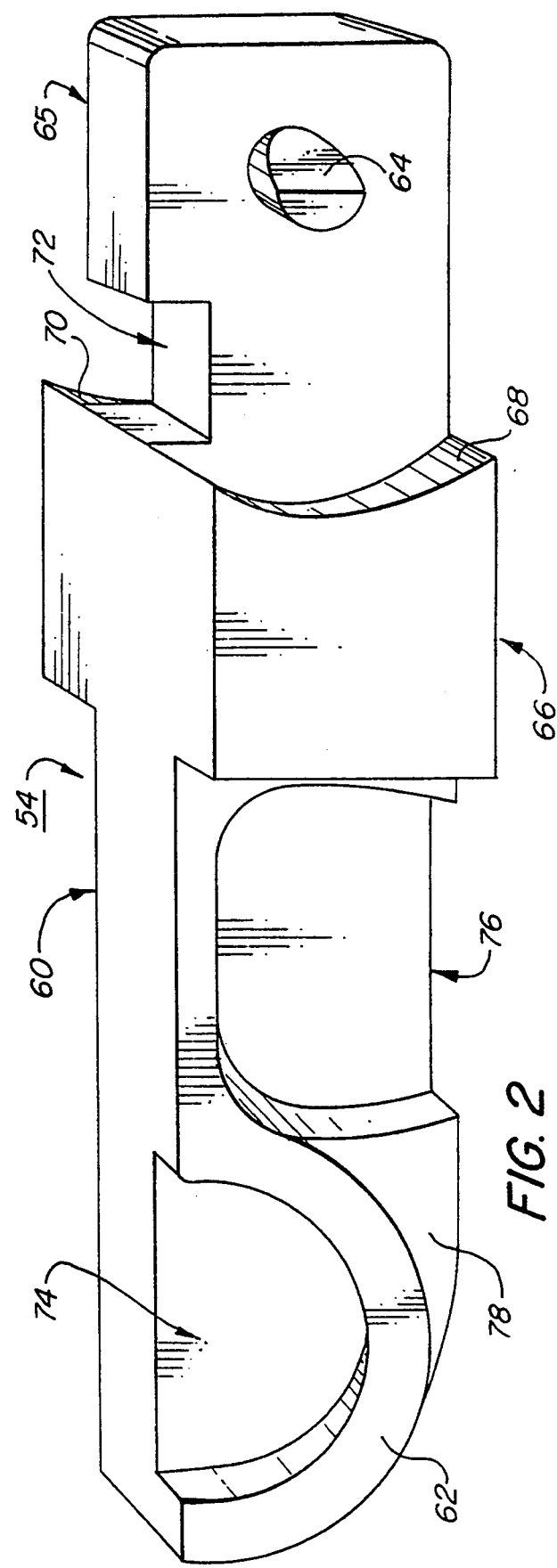

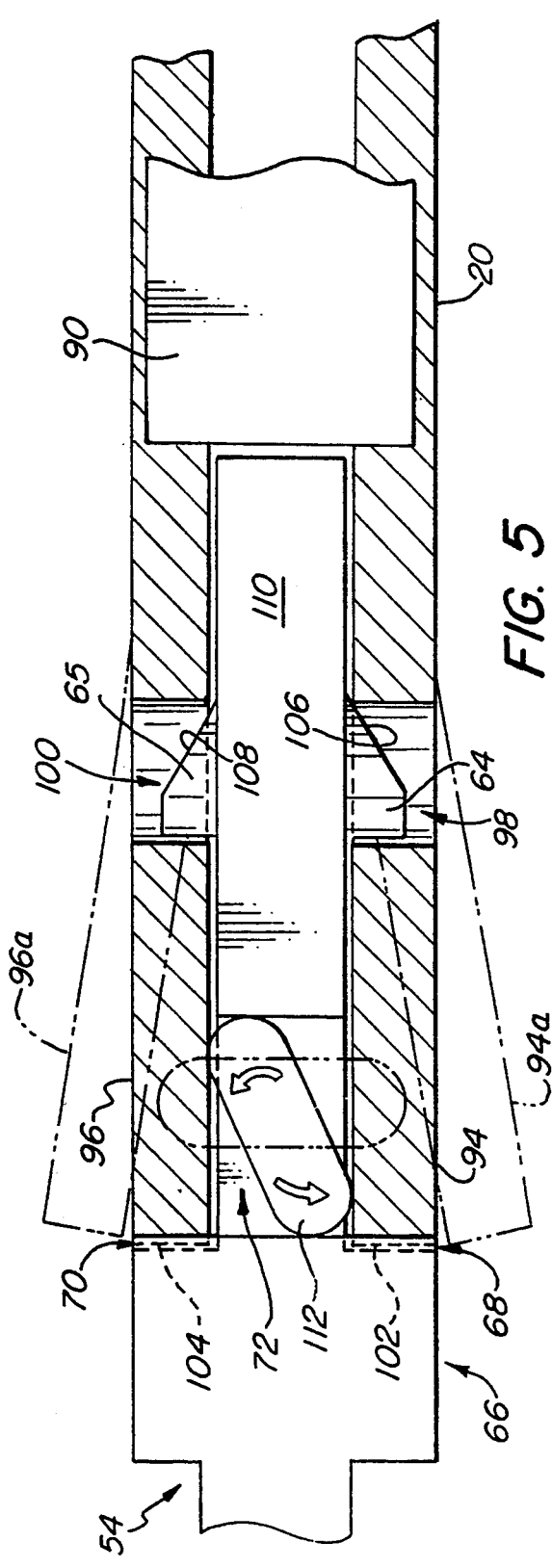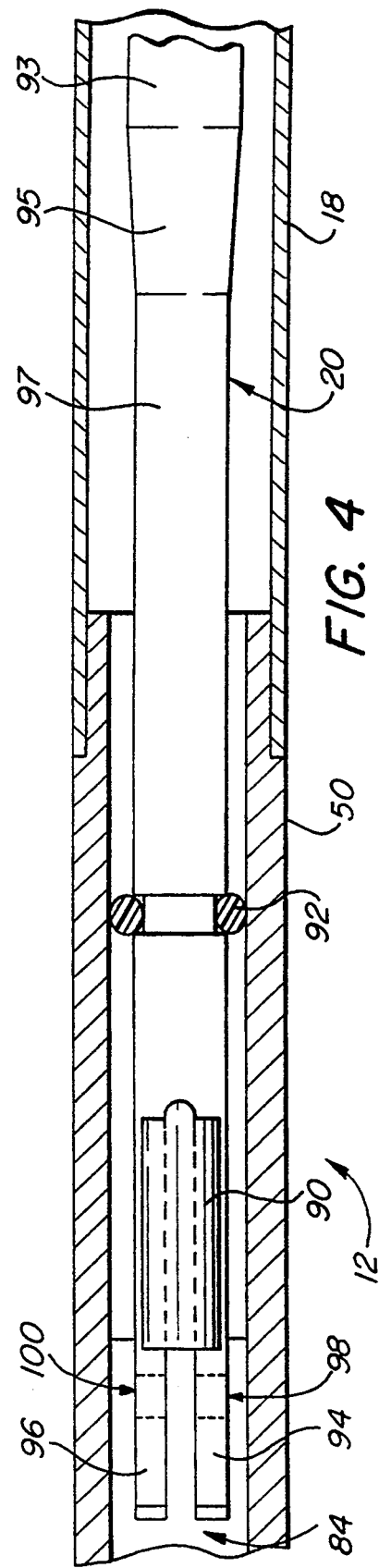

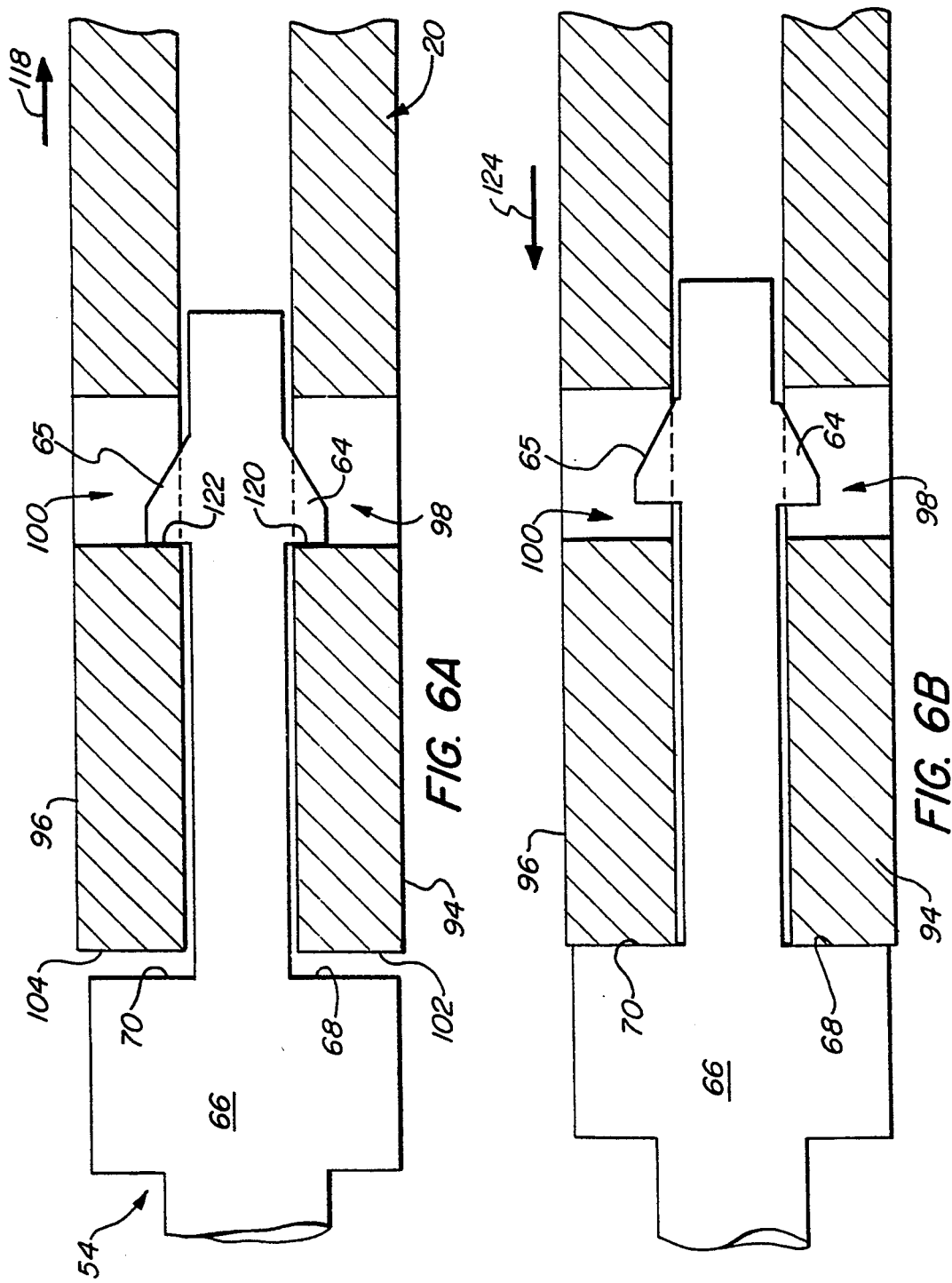

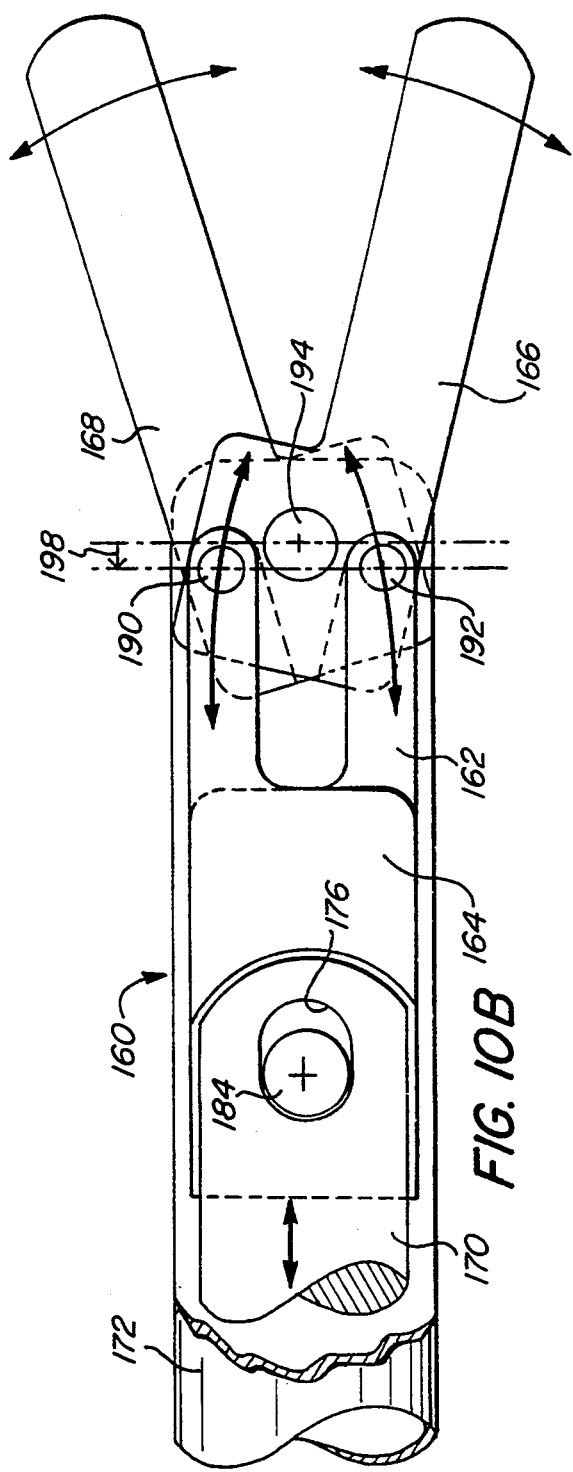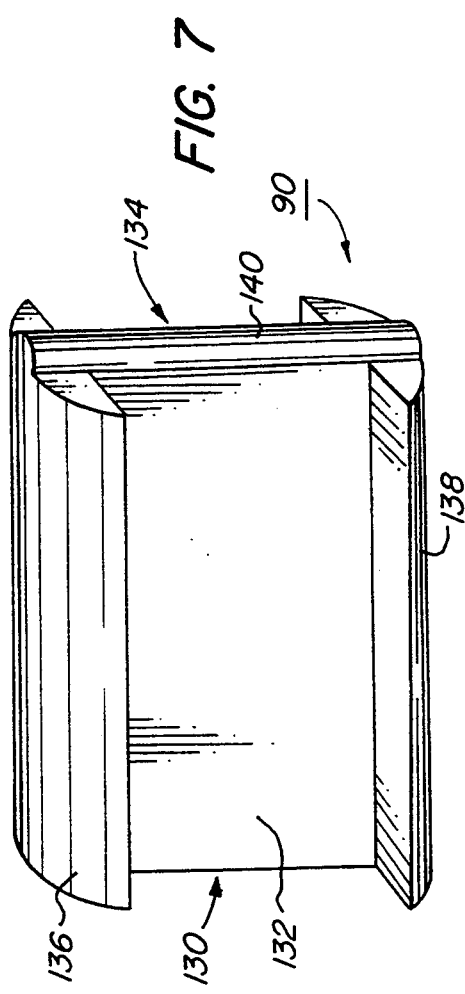

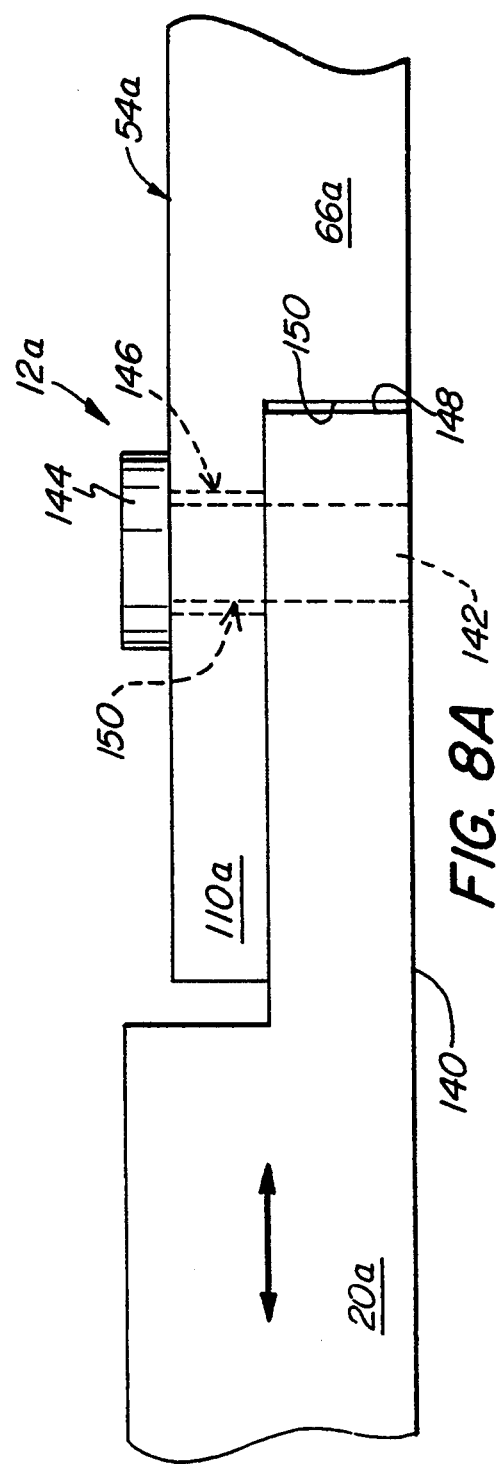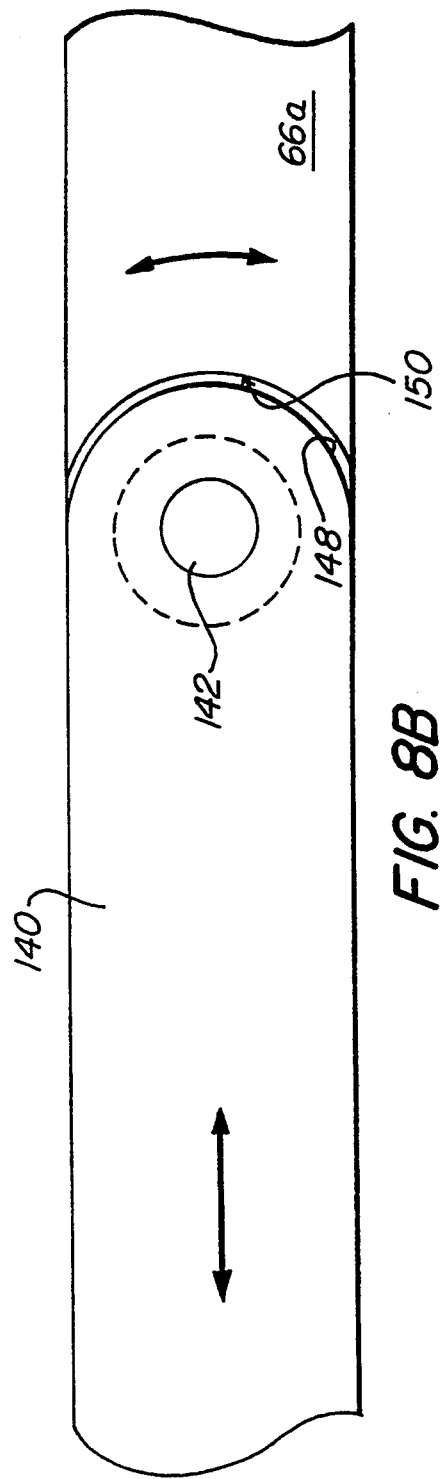

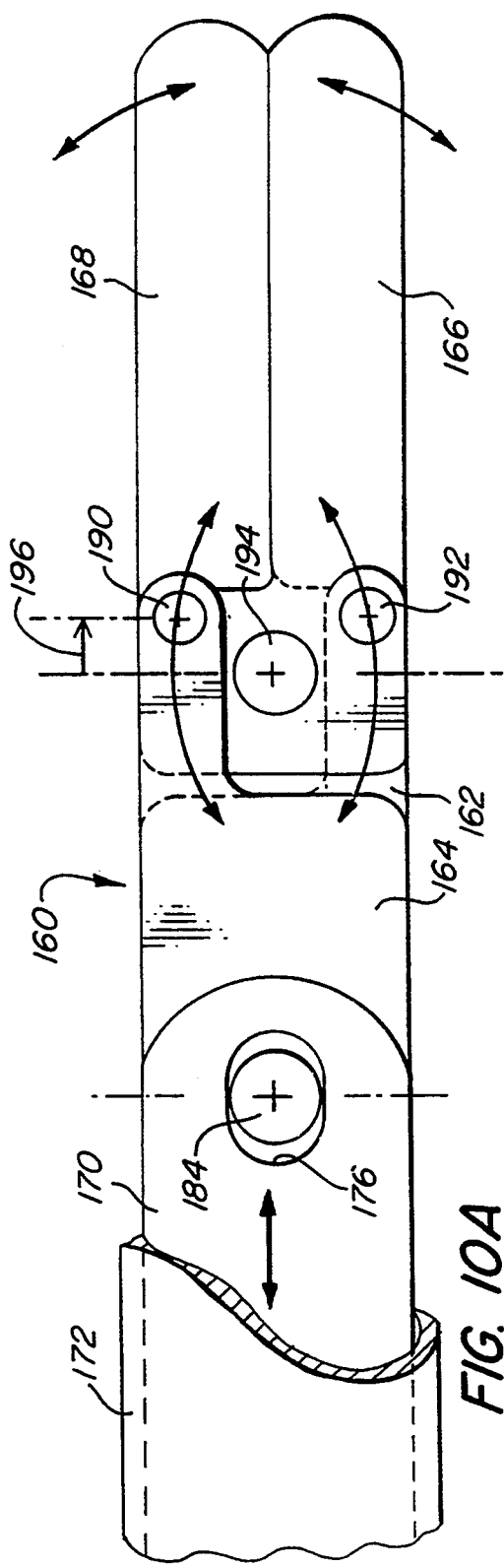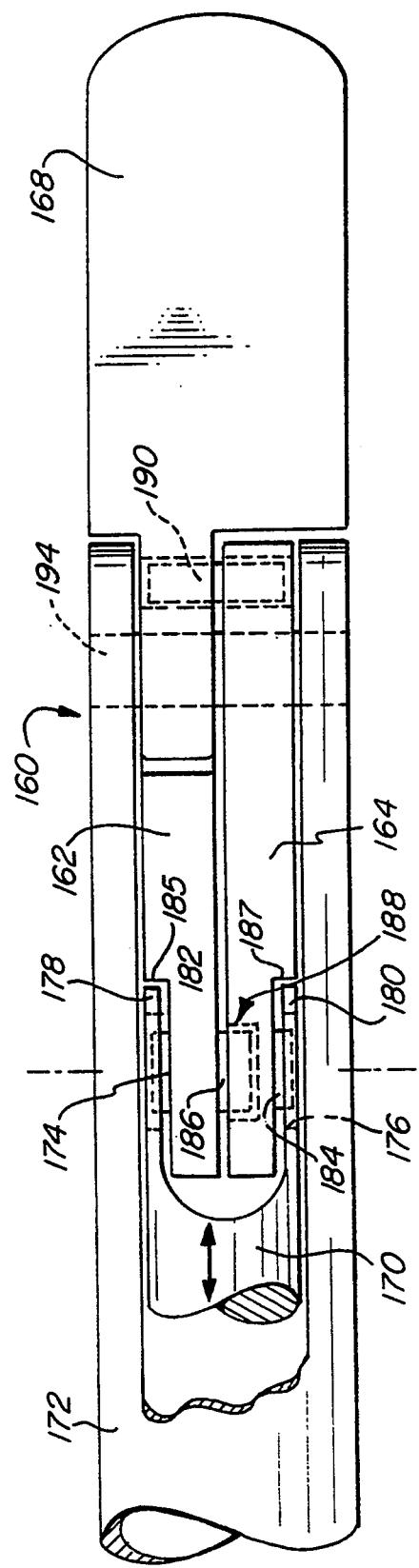

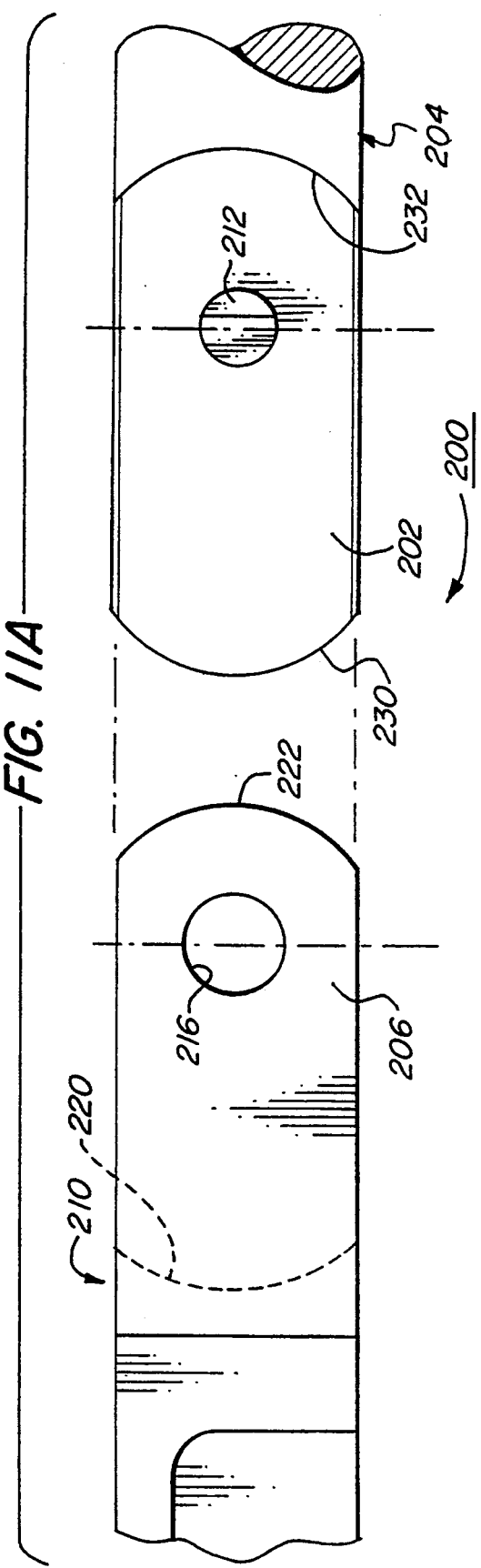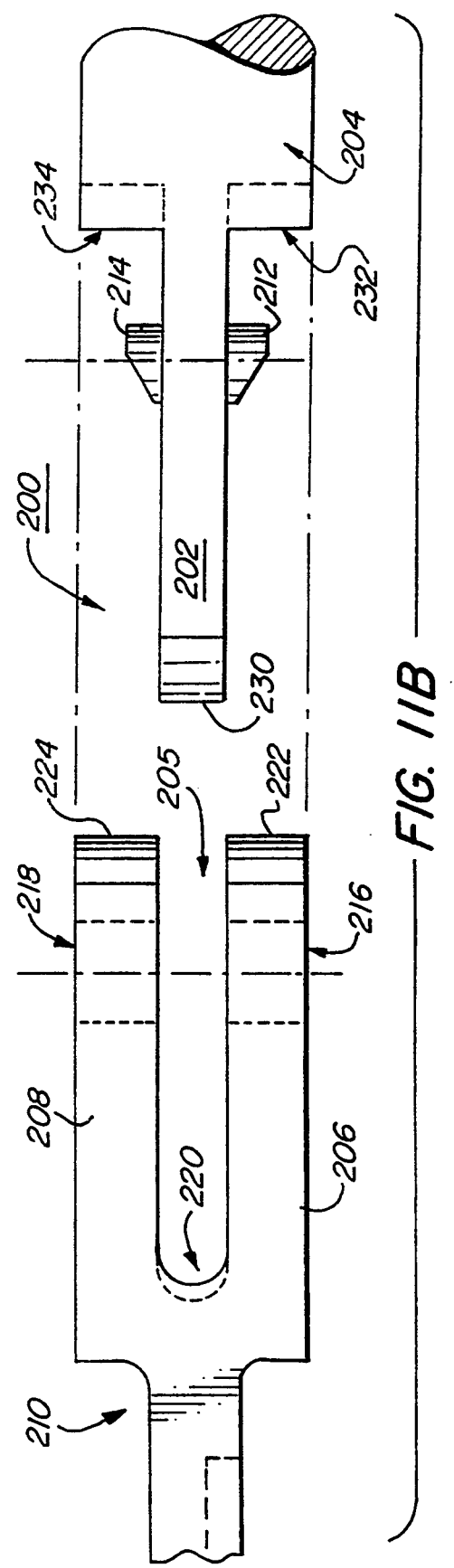

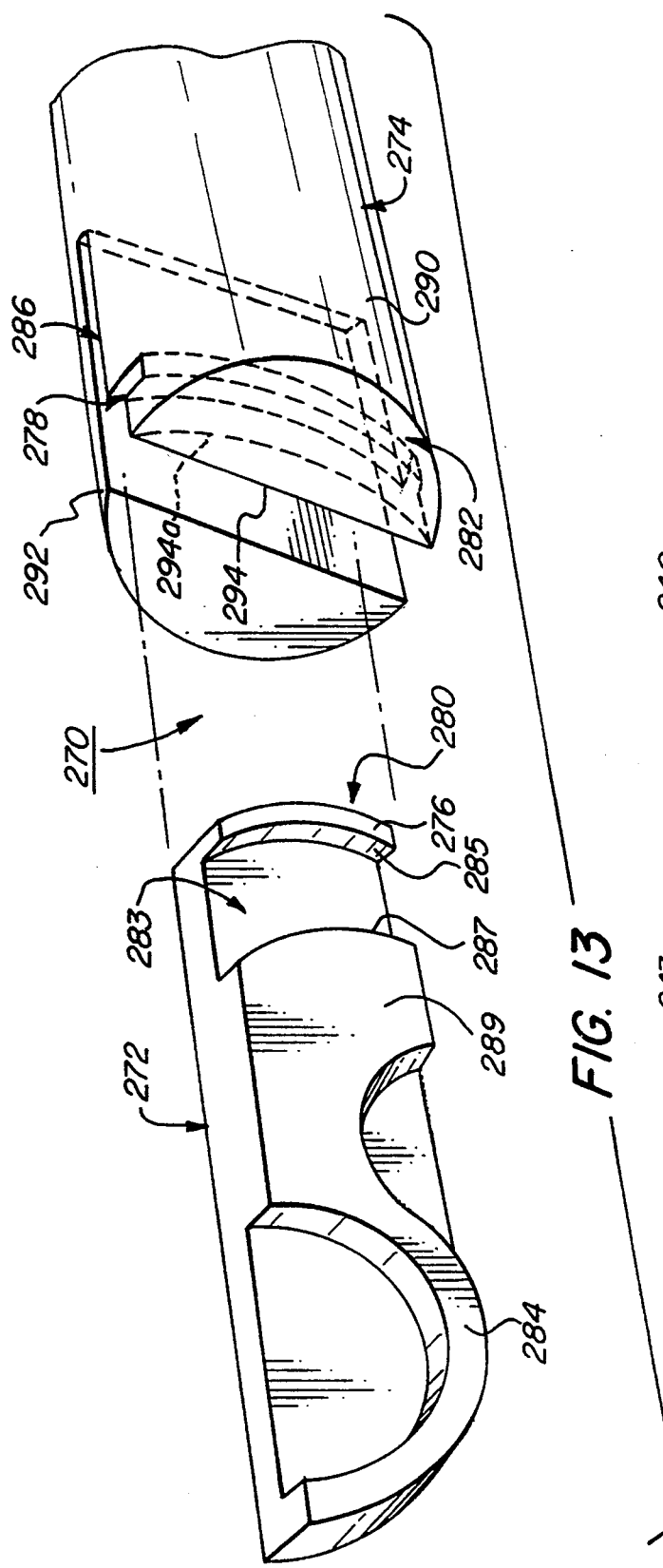
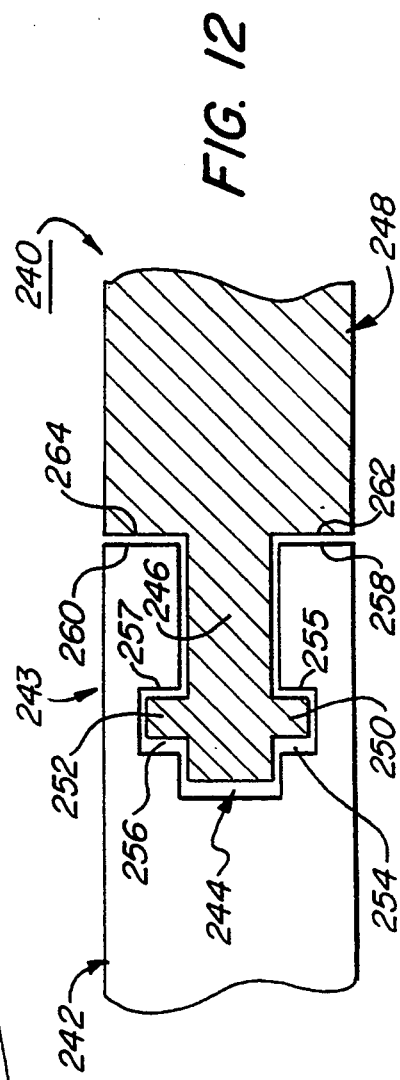
FIG. 12
FIG. 13

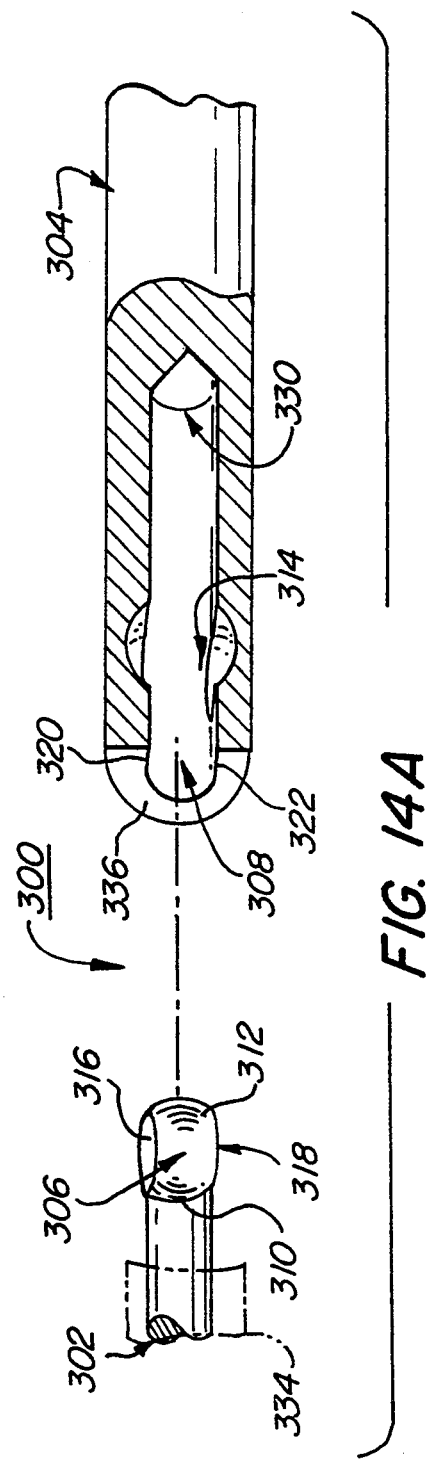

ACTUATING FORCES TRANSMISSION LINK AND ASSEMBLY FOR USE IN SURGICAL INSTRUMENTS

FIELD OF THE INVENTION

This invention relates to a linkage mechanism and assembly for transmitting first and second opposing actuating forces, and more particularly to a linkage mechanism for driving a work member, such as the jaws of a surgical forceps, between an open and a closed position.

BACKGROUND OF THE INVENTION

There are a number of instruments wherein distal jaws are remotely actuated to open and close them. A novel actuating system for a surgical instrument is described in U.S. Pat. No. 4,712,545 to Honkanen, which is commonly owned with the present invention and is incorporated herein by reference. Rather than rely on tiny pivot pins to hinge two jaws together, arcuate flanges and grooves pivotably interconnect the jaw members with a coupling member that also serves as an actuating member to drive the jaws together or apart, depending on the direction in which the coupling member is moved. Significant mechanical advantage is achieved by spreading the centers of rotation much farther apart than that which would be achieved using pivot pins mounted within the jaws.

Because the coupling member described in the Honkanen '545 Patent is a solid, rigid element which extends from the movable jaw member to a handle mechanism, the coupling member itself rises and falls over its entire length during operation of the jaws. The coupling member rises and falls within an open groove in the instrument. This is acceptable for many surgical procedures including arthroscopic knee surgery, but does not provide a fluid-tight seal between the distal and proximal ends of the instrument.

A gas-tight seal is desirable in some procedures such as laparoscopy and other surgical operations in which a pressure differential exists between the interior and the exterior of a patient. The pressure differential therefore is experienced between the distal and proximal ends of a laparoscopic instrument.

Grasper and Dissector surgical instruments for laparoscopy are available from Stryker Endoscopy, San Jose, Calif. The Stryker instruments have dual moving jaws which are connected together by a central pivot pin. Each movable jaw is separately interconnected by a pivot pin to the distal end of a link member. The two link members are interconnected at the proximal end with an actuator by a "T" projection of the actuator which fits into a recess within each link. The rise and fall motion of each link is relatively limited.

SUMMARY OF THE INVENTION

Therefore, it is one of the objects of the present invention to actuate the jaws of a surgical instrument while maintaining a gas-tight seal between the distal and proximal ends of the instrument.

It is a further object of the invention to provide a linkage mechanism which can carry an arcuate flange or groove at its distal end without defeating the gas-tight seal.

A further object of this invention is to provide a linkage mechanism which restricts rise and fall pivot action to a relatively short length of the overall instrument.

Another object of the invention is to provide such an instrument which is easy to manufacture and enables convenient and repeated assembly and disassembly.

Yet another object of the invention is to provide an improved linkage assembly which limits deformation of an O-ring.

A still further object of the invention is to provide a spacer element which further restricts rise and fall motion of a linear actuating member.

It is a further object of the invention to provide such a spacer element which occupies otherwise empty volume within the distal portion of the surgical instrument to minimize accumulation of debris.

This invention results from the realization that an improved gas-tight surgical instrument having powerful jaws can be achieved by restricting vertical rise and fall of pivoting action to a relatively short link that is movably interconnected at its distal end to a jaw member and is pivotably interconnected at its proximal end to an actuating member, and by utilizing a separate shoulder element to transmit a large force in one direction.

This invention features a link for transmitting actuating forces from an actuating member to a work member. The link includes a link body having a distal end and a proximal end. The distal end of the link body is movably interconnected with the work member by distal interconnection means such as an arcuate groove-and-flange assembly, and is interconnected at its proximal end by proximal pivotal interconnection means. The proximal means transmits a first actuating force from the actuating member to the work member. A shoulder, disposed on the link body preferably between the distal and proximal means for interconnecting, engages the actuating member when a second, greater actuating force is applied to the actuating member in a direction opposite to that of the first actuating force. The greater force is thereby transmitted to the work member.

In one embodiment, the distal interconnection means includes either an arcuate flange or an arcuate groove for interlocking with an arcuate groove or an arcuate flange, respectfully, of the work member. Alternatively, the distal interconnection means is a pivot pin. The proximal means for interconnecting may include one or more projections extending from the link body to fit within corresponding recesses in the actuating member. Preferably, the distal interconnection means and the proximal interconnection means are formed integrally with the link body, which is formed of a metal such as stainless steel.

In a preferred embodiment the shoulder includes lateral projections extending from either side of the link body, each projection defining a concave proximal end face which engages matching convex surfaces of the actuating member to enable the rise and fall pivoting action of the link. The link may further include a stop element, associated with the distal interconnection means, for limiting movement of the work member relative to the link.

This invention also features a link assembly for driving a work member, the assembly including a link as described above and an actuating member with one or two distally projecting fingers. Each finger has a distal lead surface which engages a proximal end face of the shoulder to transmit a strong pushing force.

Preferably, the link assembly is disposed within a surgical instrument having one or two movable jaws which are interconnected with one or two links that are driven by a single actuating member.

This invention additionally features a spacer member for disposition between an actuating member and an outer conduit in which the actuating member and the spacer are carried. The spacer member includes a spacer body having one or more lateral sides for engaging the actuating member, and has first and second bearing surfaces disposed on upper and lower portions of the spacer body. The bearing surfaces are shaped to slidably contact the outer conduit to assist the positioning of the actuating member relative to the outer conduit. This arrangement is particularly useful to minimize deformation of an O-ring carried by the actuating member proximal to the spacer member. A gas-tight seal is maintained thereby during actuation.

BRIEF DESCRIPTION OF THE DRAWINGS

Other objects, features and advantages will occur from the following description of a preferred embodiment and the accompanying drawings, in which:

FIG. 2 is a schematic axonometric view of the link according to the present invention;

FIG. 3 is a partial cross-sectional view of the distal portion of the surgical forceps of FIG. 1;

FIG. 4 is a schematic top cross-sectional view of the actuator disposed within the distal portion of the outer tube and the proximal portion of the stationary jaw of the instrument and carrying an O-ring and a spacer according to the present invention;

FIG. 5 is a schematic partial top plan view illustrating assembly and disassembly of the link with respect to the two distal fingers of the actuator;

FIGS. 6A and 6B are schematic top plan views showing the transmission of first and second actuation forces, respectively;

FIG. 7 is an axonometric view of the spacer of the present invention;

FIGS. 8A and 8B are schematic top and side views, respectively, of an alternative link assembly according to this invention;

FIG. 9 is a schematic partial-cross sectional top view of yet another link assembly having two links according to the present invention;

FIGS. 10A and 10B are schematic side views of the assembly of FIG. 9 in the closed and open positions, respectively;

FIG. 11A and 11B are schematic side and top views, respectively, of another link assembly according to the subject invention in which the actuator projects into a slot in the link;

FIG. 12 is a partial cross-sectional view of yet another link assembly of the present invention in which the link defines a cavity into which a portion of the actuator projects;

FIG. 13 is an axonometric view of a still further link assembly of the present invention in which the link and actuator are coupled by an arcuate groove-and-flange arrangement; and FIGS. 14A and 14B are schematic axonometric views illustrating yet another link assembly of the present invention.

DETAILED DESCRIPTION OF THE PREFERRED EMBODIMENT

Figure 1:
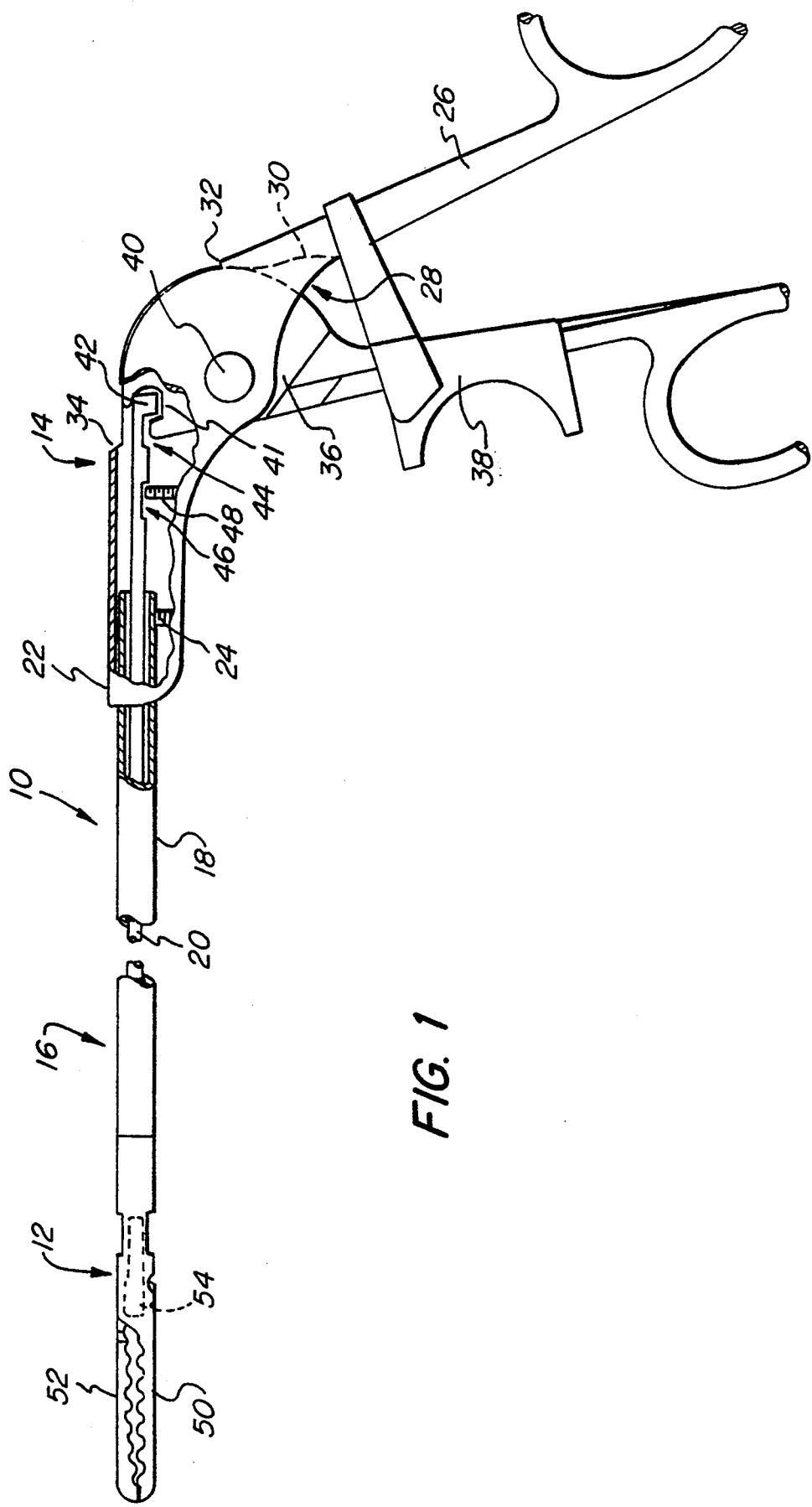
FIG. 1 is a partial-cutaway side view of a surgical forceps incorporating a link assembly according to the present invention at its distal end and an actuator drive arrangement at its proximal end.

This invention may be accomplished by a link element, and an assembly using the link element, which transmits first and second actuating forces from an actuating member to a work member such as one or more jaws of a surgical instrument. The link is movably interconnected at its distal end with the work member and is pivotably interconnected at its proximal end with the actuating member. A first actuating force is transmitted from the actuating member to the work member through a proximal interconnection element.

A second, greater actuating force is transmitted by engagement between a shoulder of the link and a distal region of the actuating member. Alternatively, alone or in combination with a shoulder, a second curvilinear surface of the proximal interconnection element receives the second actuating force. For transmission of the second force, the actuating member defines a transmitting surface having a curvature which matches that of the link's second curvilinear surface to facilitate the vertical rise and fall of the link.

The link is especially useful in minimally invasive surgery such as laparoscopy. During laparoscopy, elongated instruments are passed through an elongated cannula, and a higher pressure differential is maintained within the patient by injection of a nontoxic gas to better expose tissue for the surgeon. A link assembly according to the present invention enables an actuator member to reciprocate linearly within a gas-tight instrument shaft without defeating a seal about the actuator member.

A surgical instrument 10 according to the present invention is shown in FIG. 1 having a link assembly 12, a proximal handle assembly 14, and a central elongated section 16. The center section 16 is established by an outer conduit 18 within which an actuator rod 20 reciprocates. The proximal end of the conduit 18 is secured to a handle body 22 of the handle assembly 14 by a set screw 24. The handle body 22 is a continuous piece which terminates in an arm 26. A recess 28 is formed within the handle body 22, extending distally from a proximal edge 30, shown in phantom. The recess 28 extends completely through the upper side of the handle body 22 between a proximal point 32 and a distal point 34 to accept the upper portion of a movable arm 36.

The configuration of the handle assembly 14 in this embodiment is similar to that described in U.S. Pat. No. 4,712,545 to Honkanen, which is commonly owned and is incorporated herein by reference. When movable lock 38 is slid upwardly, the movable arm 36 can be moved distally to pivot about pivot pin 40 to drive its upper portion proximally. The upper portion of the movable arm 36 contains a rounded U-shaped recess 41 which engages a proximal projection 42 of the actuating rod 20. A proximal recess 44 is provided in the actuating rod 20 to assist engagement with the movable arm 36. A second recess 46 is provided in the actuating rod 20 to receive a set screw 48 which serves as a stop to limit the reciprocating motion of the actuating rod 20.

The link assembly 12 in this embodiment comprises a stationary lower jaw 50 which is attached by soldering or welding to the distal portion of the conduit 18, and an upper movable jaw 52. The jaws 50, 52 serve as a toothed grasper in this construction; alternatively, other types of jaws for forceps, punches or other instruments can be utilized such as described in the Honkanen '545 patent.

The movable jaw 52 is interconnected with the actuating rod 20 by a link 54 according to the present invention, indicated in a phantom in FIG. 1. The link 54 is shown in greater detail in FIG. 2 after disassembly from the instrument 10. The link 54 includes a link body 60 having an arcuate flange 62 at its distal end for interconnection with the movable jaw 52, FIG. 1, and opposing projections 64, 65 for interconnection with the actuating rod 20 as described in more detail below.

The link 54 further includes an integral shoulder 66, FIG. 2, which projects laterally to either side of the link body 60. The shoulder 66 defines proximal curvilinear end faces 68, 70 which engage with the distal leading surfaces of the actuating rod 20, again as described in more detail below. Also described below is the function of a notch 72 during disassembly.

The interconnection of the arcuate flange 62 with a corresponding groove in the movable jaw is similar to that described in the Honkanen '545 patent in which the distal end of the continuous coupling member carries an arcuate flange or groove. In contrast, the link 54 is a separate member which carries the movable interconnection element in the present invention.

The arcuate flange 62 is formed by milling a semi-circular recess 74 in the upper distal portion of the link body 60. A separate recess 76 is milled in an inverted U-shape proximal to the flange 62 to receive the proximal portion of the movable jaw 52. A triangular portion 78 remains extending from the link body 60 to serve as a stop to limit the angle of opening of the movable jaw.

The link assembly 12 is shown in greater detail in FIG. 3. The left side of the stationary jaw 50 and the outer conduit 18 have been cut away for illustration purposes. The flange 62 of the link 54 is shown interlocked with a matching groove 80, shown in phantom, which is formed within the movable jaw 52. The stationary jaw 50 and the movable jaw 52 are pivotably interconnected by a pair of arcuate flanges and grooves, represented by arc 82, shown in phantom.

The stationary jaw 50 defines lower and upper slots 84, 86, respectively, through which movable jaw 52 and the link 54 are assembled and disassembled as described below. Also shown is a portion of a spacer 90 according to the present invention and an O-ring 92 which establishes a seal between the actuator rod 20 and the proximal cylindrical portion of the stationary jaw 50. Approximately one-eighth inch of the outer proximal surface of the stationary jaw 50 has been milled to fit within the distal end of the conduit 18.

A top view of the link assembly 12 with the link 54 removed is shown in FIG. 4. The actuating rod 20 in this construction tapers from a large-diameter region 93 to a narrow diameter region 97 through a transition region 95. The actuator rod 20 terminates distally in a pair of fingers 94, 96 which define lateral openings 98, 100, respectively.

The interconnection of the link 54 with the distal fingers 94, 96 is schematically shown in FIG. 5. The convexly curved distal lead surfaces 102, 104 of the distal fingers 94, 96 are shown contacting the concave surfaces 68, 70 of the shoulder 66. The corresponding convex and concave surfaces enable unrestricted rise and fall of the link 54 relative to the actuator rod 20.

The projections 64, 65 have slanted proximal surfaces 106, 108 to assist insertion past the distal lead surfaces 102, 104 of the fingers 94, 96. Alternatively, the inner edges of the fingers 94, 96 are chamfered along the vertical axis as well as being convex along the horizontal axis.

During assembly, the movable jaw 52, FIG. 3, is inserted through upper slot 86 to engage the lower arcuate flange-and groove arrangement indicated as arc 82. After jaw 52 has been interconnected with the stationary jaw 50, the arcuate flange 62 of the link 54 is interconnected with the corresponding groove 80 of jaw 52. The link 54 is brought to rest in a horizontal position as shown in FIG. 3. The actuator rod 20 is then inserted distally through the conduit 18 so that a proximal shaft portion 110 of the link 54 slides between the distal fingers 94, 96 until the projections 64, 65 snap into the openings 98, 100.

During disassembly, the fingers 94, 96 must be spread apart so that the distal surfaces of the link projections 64, 65 clear the edges of the openings 98, 100. To accomplish this, a blade 112 having a rectangular or elliptical cross-section is inserted into the slot 72. The blade 112 is rotated to place the blade 112 perpendicular to the fingers 94, 96 which cams them apart as indicated in the phantom by lines 94a, 96a. The link 54 is then moved distally and upwardly to disengage it from the fingers 94a, 96a, or the actuating rod 20 is drawn proximally.

The transmission of actuation forces from actuating rod 20 to link 54 is shown schematically in FIGS. 6A and 6B. When the actuating rod 20 is pulled proximally as shown by arrow 118, the distal surfaces 120, 122 of the link projections 64, 65 engage the distal surfaces of the finger openings 98, 100. The link 54 is thereby pulled proximally to open the jaw 52 relative to the stationary jaw 50.

The distal surfaces 120, 122 are curved in a preferred embodiment as shown in FIG. 2 even though they appear flat in cross-section as shown in FIGS. 6A and 6B. Surfaces 120, 122 serve as first curvilinear surfaces for receiving the first, pulling actuating force.

Greater power is required during closing of the jaws. To accomplish the transfer of a large amount of closing force, the openings 98, 100 are somewhat oversized, especially along the longitudinal axis to allow the distal lead surfaces 102, 104 of the fingers 94, 96 to directly engage the shoulder curvilinear surfaces 68, 70 when the actuating rod 20 is pushed distally in the direction indicated by arrow 124.

Therefore, two different loci of force transfer, or alternating load-bearing surfaces, are accomplished with the present invention. Preferably, the force transfer surfaces are curved to facilitate the pivoting action of the link relative to the actuator.

The spacer 90, which is shown in previous figures but is omitted in FIGS. 6A and 6B, is shown separately in greater detail in FIG. 7. The spacer 90 is comprised of a spacer body 130 having flattened lateral surfaces 132, 134 which contact the inner lateral surfaces of the distal fingers 94, 96. Upper and lower bearing surfaces 136, 138 respectively, extend over and under the fingers 94, 96 as illustrated in FIG. 4. The bearing surfaces 136, 138 are arcuate to match the curvature of the conduit 18.

The spacer 90 assists restriction of the vertical rise and fall motion occurring within the link assembly 12 to the link 54 alone. The spacer 90 therefore aligns and positions the actuating rod 20 relative to the outer conduit 18 and provides a bearing surface against the inner surface of the conduit 18. These advantages are achieved without relying on the O-ring 92. In fact, spacer 90 minimizes deformation of the O-ring to maintain a gas-tight seal.

Additionally, the spacer 90 occupies volume that would otherwise be empty to prevent trapping and build-up of debris or other material within the space between the fingers 94, 96. Where the fingers 94, 96 meet at a rounded junction, as in the present construction, the spacer 90 includes a proximal rounded projection 140, FIG. 7 which nestles into the junction to further occupy volume and to assist positioning on the spacer 90 relative to the fingers 94, 96.

Other configurations of spacer 90 will be apparent for other spatial relationships between the actuator 20 and the conduit 18. For example, upper and lower bearing surfaces 136, 138 can be extended toward each other to form a cylinder. One or more lateral slits can be provided to allow a spreading apart of the distal fingers of the actuator during disassembly.

Preferred approximate dimensions and materials for several components for one construction of the surgical instrument 10 are as follows. The jaws 50, 52 and the link 54 are formed of 17-4PH (precipitation hardness) stainless steel which is readily available commercially. The link 54 has an overall length of 0.49 inch and a maximum height of 0.09 inch. The distal portion of the link 54 has a greatest width of 0.030 inch while the shoulder 66 has a maximum width of 0.58 inch and the proximal portion 110 has a width of 0.025 inch. The link projections 64, 65 have an overall diameter of 0.030 inch and project approximately 0.010 inch from the sides of proximal portion 110. The notch 72 has a length of 0.040 inch.

The actuator 20 is preferably formed of an elastic material such as custom 455 stainless steel available from Carpenter Stainless Steel of Reading, Penna. The elasticity allows repeated spreading and closing of the distal fingers 94, 96 to allow assembly and disassembly as desired. The actuator 20 has an overall length of approximately 14.9 inch while the fingers 94, 96 have an overall length of 0.31 inch. The openings 98, 100 are 0.031 inch diameter holes. The full-diameter portion 93 of the actuator member 20 is a rod having a diameter of 0.58 inch which tapers to narrow region 97 having a diameter of 0.72 inch.

In other embodiments, the openings 98, 100 and the link projection 64, 65 can be oblong, elliptical, rectangular or square, or different combinations thereof. Further, the openings 98, 100 can be partial recesses rather than complete through-holes. The relative shapes of the link projection 64, 65 and the openings 98, 100 can be selected to limit the rise and fall of the link 54 relative to the actuator member 20. For example, flat surfaces can be provided at the corners of a rectangular square projection to engage the upper surface of a rectangular opening to limit upward pivoting motion.

To assist assembly and disassembly, the upper lateral surfaces of the fingers 94, 96 and/or the upper surface of the proximal portion 110 can be chamfered in the region of notch 72 to provide two "V" angles into which two blades can be inserted parallel to the fingers 94, 96 to assist spreading during disassembly.

The spacer 90 is formed of DELRIN polyacetal. It has an overall length of 0.172 inch and a diameter of 0.089 inch. The spacer body 130 has a width of 0.023 inch. The O-ring is formed of 95% silicone and 5% Teflon. Both DELRIN polyacetal and the silicone/Teflon compositions have low coefficients of friction.

The conduit 18 is stainless steel tubing of 303 or 304 stainless steel. The handle arms 36, 26 and handle body are formed of 303 stainless steel.

The placement of a flange or a groove on the stationary member 50 in the position indicated as arc 82 in FIG. 3 depends upon the wall thickness of the jaw 50 and whether, during use, the walls tend to be forced apart from each other. A straight-sided flange placed on the outer stationary jaw member walls is preferred in most circumstances for ease of manufacture, but a dovetail arrangement is useful to resist lateral spreading of the jaw walls.

The projections 64, 65 of link 54 are preferably formed integrally by milling with circular interpolation to form the projections. In other constructions, the projections 64, 65 can be established by a pin which is fitted through a hole in the side of proximal portion 110. The integrally-formed projections are desired because the problems of edge .load of a pin on the rims of a hole are avoided. Edge load is particularly important for a smaller-sized instruments.

An alternate link assembly suited for larger-sized instruments is shown in FIGS. 8A and 8B. Link assembly 12a is an alternative hinge-type arrangement which includes a link 54a having a proximal portion 110a that lies against single distal finger 140 of an actuator member 20a. The actuator member 20a and the link 54a are pivotably interconnected by a pivot pin 142 which is threaded, pressed, or otherwise secured to the finger 140. A head 144 prevents the proximal portion 110a from separating laterally away from the finger 140. The proximal portion 110a defines an over-sized hole 146 which enables the alternate transmission of forces at different loci according to the present invention.

When actuator 20a is advanced toward the link 54a, the distal lead surface 148 contacts the proximal surface 150 of the shoulder 66a. When the actuator 20a is pulled proximally, the proximal surface of the hole 146 contacts the proximal surface 150 of the pin 142. The contacting surfaces 148, 150 are curved relative to each other as shown in FIG. 8B to provide unrestricted pivoting action.

An alternate link assembly 160 is shown in FIGS. 9-10B having two links 162, 164 which are attached to movable jaws 166, 168, respectively. The link assembly 160 is shown in a closed position in top view in FIG. 9 and in side view in FIG. 10A. An actuator rod 170 reciprocates within an outer tube 172. Elliptical openings 174, 176 are defined in distal fingers 178, 180, respectively, of the actuator 170. A projection 182 of the link 162 extends into the opening 74 and a projection 184 of the link 164 extends into the opening 176. The links 162, 164 are interconnected at their center by a projection 186 of link 162 which extends into recess 188 of link 164.

In the closed position shown in FIGS. 9 and 10A, the leading distal edges of the fingers 178, 180 contact corresponding shoulders 185, 187 of links 162, 164. The distal end of link 164 is interconnected with upper jaw 168 by a pin 190 whereas the link 164 is interconnected with lower jaw 166 by a pin 192. The jaws 166, 168 are interconnected with each other by a central pivot pin 194 which extends through corresponding holes in the outer tube 172. Pivot pins 190, 192 lie distal to the central pin 194 as indicated by arrow 196.

When the actuator 170 is pulled proximally, the link projections 182, 184 contact the proximal edges of the openings 174, 176 to drive jaws 166, 168 in opposite directions as shown in FIG. 10B. The pivot pins 190, 192 are pulled proximal to the central pin 194 as indicated by arrow 198. Therefore, the reciprocation of a single actuator can drive two movable jaws when two links are used according to the present invention. As is exhibited in the previously-described embodiments, the actuator directly contacts shoulders of the links to drive the jaws to a closed position while separate projections on the links engage different portions of the actuator to drive the jaws open.

An alternative link assembly 200, FIGS. 11A–11B, includes a tang 202 of an actuator rod 204 which projects into a slot 205 defined by prongs 206, 208 of a link 210. The tang 202 carries projections 212, 214 which engage recesses 216, 218 of the prongs 206, 208. The link 210 defines one concave shoulder 220 at the junction of the prongs 206, 208 and two convex shoulders 222, 224 which are defined by the proximal ends of the prongs 206, 208. The actuator 204 defines matching convex surface 230 and concave surfaces 232, 234, respectively.

Yet another link assembly 240 is shown in FIG. 12 having a link 242 with a proximal portion 243 which defines a cavity 244 into which a tongue 246 of an actuator 248 is inserted. The tongue 246 defines curvilinear projections 250, 252 that fit within matching recesses 254, 256, respectively. Curvilinear link surfaces 255, 257 of the proximal portion 243 engage the actuator projections 250, 252 when a first, pulling actuating force is applied to the actuator 248.

The recesses 254, 256 are somewhat oversized, at least in the longitudinal direction, to enable the projections 250, 252 to move distally when the actuator 240 is pushed in the opposite direction. The shoulders 258, 260 of the link 242 then contact matching surfaces 262, 264, respectively, of actuator 248. The pairs of surfaces 258, 260 and 262, 264 are correspondingly concave and convex, or convex and concave.

The link assembly 240 is assembled and disassembled in a bayonet-type fashion: a cavity 244 is sloped and twisted so that the actuator 248 must be rotated ninety degrees during insertion and removal.

FIGS. 13 and 14A–14B illustrate two additional embodiments in which a link is insertable into an actuator rod and vertical rise and fall is restricted to the link. Both links define a proximal element having a first curvilinear face for pivotably engaging a first surface of an actuating member to transmit a first actuating force from the actuating member to a work member such as a movable jaw. The proximal element also has a second curvilinear face for pivotably engaging a second surface of the actuating member to transmit a second, greater actuating force applied to the actuating member in direction opposite to that of the first actuating force to transmit the second force to the work member.

Link assembly 270, FIG. 13, has a link 272 which pivotably engages an actuator 274. The link 272 has an arcuate flange 276 which engages an arcuate groove 278 of the actuator 274. The link 272 further includes a distal interconnection element such as arcuate flange 284 as shown.

The arcuate groove 278 extends laterally from a slot 286 in the actuator 274 which enables distal sections 290, 292 to spread apart to receive the proximal end of the link 272 so that it can be longitudinally snapped into the actuator 274. A portion of a proximal shoulder face 280 of the link 272 or a leading edge 294 of the actuator 274 can be chamfered to assist the insertion of the link 272 into the actuator 274.

The distal surface of the groove 278 contacts the first curvilinear link face 285 to transmit a first, pulling actuating force. The proximal surface of the groove 278 contacts the second curvilinear link face 280 to transmit the second, greater pushing actuating force.

A channel 283 has a sufficient length along the longitudinal axis to maintain the proximal face 287 of the link body 289 away from the distal face 282 of the link 274. Alternatively, the channel 283 is shorter to allow the face 287 to serve as a shoulder to receive the pushing actuation force. In the alternative construction the face 282 is concave, as indicated in phantom by edge line 294a.

The slot 286 is exaggerated for the purposes of illustration; preferably it is narrow and located relative to the central longitudinal axis of the actuator 274 so that force is directed as on-center as possible to the proximal face 280 of the link 272.

Link assembly 300, FIGS. 14A–14B, comprise a link 302 having a substantially spherical, ball-like proximal end 306 which is insertable into recess 308 of an actuator 304. The spherical end 306 includes a first curvilinear surface 310 and a second curvilinear surface 312 which contacts the distal and proximal surfaces of spherical chamber 314 extending from the recess 308. The spherical end 306, also referred to as a protuberance, has flat surfaces 316, 318 which slide past flattened surfaces 320, 322, respectively, at the entrance to the recess 308. Once the link 302 is inserted so that the protuberance 306 has entered the chamber 314, the link 302 is rotated ninety degrees to the position shown in FIG. 14B.

The link 302 is formed as an integral piece which initially has an outer diameter corresponding to that of the protuberance 306. A main shaft 324 is ground down by milling, followed by formation of haft 326 which terminates in arcuate flange 328 for interconnection with a work member such as a movable jaw. The recess 308, including the chambers 314 and 330, are formed by boring. This embodiment further includes a spring chamber 330 in which a spring 332 is disposed to minimize possible vibrations and to improve the "feel" of the instrument during actuation. Preferably, different alloys of stainless steel are used as the materials for the above-identified components when used in a surgical instrument.

During actuation, a pulling force is transmitted to the link 302 by contact with the first surface 310, and a second greater force can be transmitted to the link 302 by contact of the proximal surface of the chamber 314 with the second curvilinear surface 312. Alternatively, a shoulder 334, shown in phantom, can be added to contact the distal face 336 of the actuator 304 to transmit the pushing force. Preferably, both the proximal surface of the shoulder 334 and the face 336 are curved in a mating fashion to facilitate vertical rise and fall of the link 302. The chamber 314 in the alternative construction is sufficiently oversized, at least in the longitudinal direction, to enable contact between the proximal surface of the shoulder 334 and the distal actuator face 336.

Although specific features of the invention are shown in some drawings and not in others, this is for convenience only as each feature may be combined with any or all of the other features in accordance with the invention.

Other embodiments will occur to those skilled in the art and are within the following claims.

What is claimed is:

1. A link for-transmitting actuating forces from an actuating member to a work member, comprising:
 a link body having a distal end and a proximal end;
 distal means, disposed proximate to said distal end of said link body, for movably interconnecting said link body with the work member;
 proximal means, disposed proximate to said proximal end of said link body, for pivotally interconnecting said link body with the actuating member, and for transmitting a first actuating force from the actuating member to the work member; and
 a shoulder, formed as an integral part of said link body longitudinally spaced from said proximal means for interconnecting, for engaging a distal region of the actuating member when a second, greater actuating force is applied to the actuating member in a direction opposite to that of said first actuating force to transmit said second force to the work member, said shoulder including at least one lateral projection extending from at least one side of said link body, said projection defining a proximal end face engageable with the distal region of the actuating member.

2. The link of claim 1 in which said proximal means for interconnecting includes at least one projection capable of fitting within a corresponding recess in the actuating member, 3. The link of claim 2 in which said projection is formed as an integral part of said link body, 4. The link of claim 1 in which said shoulder is attached to said link body between said distal and proximal means for interconnecting.

5. The link of claim 1 in which said proximal means for interconnecting is constructed to transmit a pulling force from the actuating member to drive the work member proximally toward the actuating member.

6. The link of claim 5 in which said shoulder is configured to transmit a pushing force toward the work member to drive the work member distally.

7. The link of claim 1 in which said shoulder includes lateral projections extending from either side of said link body, each projection defining a proximal end face.

8. The link of claim 7 in which said proximal end faces are concave for slidably engaging matching convex surfaces of the distal region of the actuating member.

9. A link assembly for driving a work member, comprising:
 a link body having a distal end and a proximal end;
 distal means, attached proximate to said distal end of said link body, for movably interconnecting said link body with the work member;
 an actuating member having a first distal region and a second distal region;
 proximal means, attached proximate to said proximal end of said link body, for pivotally interconnecting said link body with said actuating member at said first distal region, and for transmitting a first actuating force from said actuating member to the work member;
 a shoulder, disposed on said link body between said distal and proximal means for interconnecting and longitudinally spaced from said proximal means for interconnecting, for engaging said second distal region of said actuating member when a second, greater actuating force is applied to said actuating member in a direction opposite to that of said first actuating force to transmit said second force to the work member; and
 said actuating member including at least one distally projecting finger, said finger having a distal lead surface which serves as said distal region for engaging said shoulder of .said link, and said finger further defining a recess proximal to said distal lead surface for interlocking with said proximal means for pivotally interconnecting.

10. The link assembly of claim 9 in which said actuating member includes two spaced distally projecting fingers.

11. The link assembly of claim 10 in which said shoulder includes lateral projections extending from either side of said link body, each projection defining a concave proximal end face, and each finger having a matching convex distal lead surface.

12. The link assembly of claim 11 in which said distal means, said proximal means, and said shoulder are formed integrally with said link body.

13. The link assembly of claim 12 in which said proximal means for interconnecting includes a projection extending from either side of said link body and each said distal finger includes a corresponding recess for receiving the respective projection.

14. A surgical instrument comprising:
 a first movable jaw member;
 a second jaw member;
 a conduit having an inner passage extending through it;
 an actuating member having a first distal region and a second distal region, and slidably disposed within said conduit;
 a first link body having a distal end and a proximal end;
 distal means, attached proximate to said distal end of said link body, for movably interconnecting said link body with said first movable jaw member;
 proximal means, attached proximate to said proximal end of said first link body, for pivotally interconnecting said first link body with said actuating member at said first distal region, and for transmitting a first actuating force from said actuating member to said first movable jaw member; and
 a shoulder, disposed on said link body longitudinally spaced from said proximal means for interconnecting, having a curvilinear surface for engaging said second distal region of said actuating member when a second, greater actuating force is applied to said actuating member in a direction opposite to that of said first actuating force to transmit said second force to said first movable jaw member.

15. The surgical instrument of claim 14 in which said shoulder is attached to said link body between said distal and proximal means for interconnecting.

* * * * *